(12) United States Patent
Ludensky et al.

(10) Patent No.: US 7,407,590 B2
(45) Date of Patent: Aug. 5, 2008

(54) METHOD FOR REMOVAL OF BIOFILM (75) Inventors: Michael Ludensky, Randolph, NJ (US); Philip G. Sweeny, Hackettstown, NJ (US)

(73) Assignee: Lonza, Inc., Fair Lawn, NJ (US)

( * ) Notice: Subject to any disclaimer, the term of this patent is extended or adjusted under 35 U.S.C. 154(b) by 0 days.

(21) Appl. No.: 10/540,293

(22) PCT Filed: Jun. 6, 2003

(86) PCT No.: PCT/US03/17882

§ 371 (c)(1), (2), (4) Date: Jul. 20, 2005

(87) PCT Pub. No.: WO2004/060818

PCT Pub. Date: Jul. 22, 2004

(65) Prior Publication Data

US 2006/0049119 A1 Mar. 9, 2006

Related U.S. Application Data (60) Provisional application No. 60/435,680, filed on Dec. 20, 2002.

(51) Int. Cl.
*C02F 1/76* (2006.01)

(52) U.S. Cl. .............. 210/698; 162/161; 210/631; 210/755; 210/756; 210/764; 422/16; 422/37

(58) Field of Classification Search .............. 210/755
See application file for complete search history.

(56) References Cited

U.S. PATENT DOCUMENTS 3,328,294 A 6/1967 Self et al.
3,749,672 A 7/1973 Golton et al.
4,235,599 A 11/1980 Davis et al.
4,297,224 A 10/1981 Macchiarolo et al.
4,382,799 A 5/1983 Davis et al.
4,427,692 A 1/1984 Girard (Continued)

FOREIGN PATENT DOCUMENTS

EP 0 137 875 A1 4/1985

(Continued)

OTHER PUBLICATIONS

Chemical Abstracts, vol. 95, No. 4 (1981), Abstract No. 30168q.

(Continued)

*Primary Examiner*—Peter A. Hruskoci
(74) *Attorney, Agent, or Firm*—Darby & Darby PC; Shelly M. Fujikawa (57) ABSTRACT

The present invention provides a method for the removal of biofilm, flocculent bulked sludge or bulked biologically active sludge from an aqueous system. The method involves adding one or more chlorinated hydantoins, such as dichloro- or monochlorodialkylhydantoin, to the aqueous system. Alternatively, the chlorinated hydantoin may be formed in situ by adding a chlorine source and an alkylated hydantoin separately to the aqueous system. The invention is particularly advantageous because of the outstanding photostability of the chlorinated hydantoin solutions even when exposed to sunlight.

17 Claims, 5 Drawing Sheets

U.S. PATENT DOCUMENTS

| | | | |
|---|---|---|---|
| 4,537,697 | A | 8/1985 | Girard |
| 4,560,766 | A | 12/1985 | Girard et al. |
| 4,561,981 | A | 12/1985 | Characklis |
| 4,654,424 | A | 3/1987 | Girard et al. |
| 4,698,165 | A | 10/1987 | Theyson |
| 4,925,866 | A | 5/1990 | Smith |
| 4,976,874 | A | 12/1990 | Gannon et al. |
| 5,071,765 | A | 12/1991 | Wiatr |
| 5,565,109 | A | 10/1996 | Sweeny |
| 5,565,576 | A | 10/1996 | Hall et al. |
| 5,603,941 | A * | 2/1997 | Farina et al. ............... 424/405 |
| 5,662,940 | A | 9/1997 | Hight et al. |
| 5,750,061 | A | 5/1998 | Farina et al. |
| 5,972,864 | A | 10/1999 | Counts |
| 5,976,386 | A | 11/1999 | Barak |
| 6,132,628 | A | 10/2000 | Barak |
| 6,149,835 | A | 11/2000 | Brown |
| 6,267,897 | B1 | 7/2001 | Robertson et al. |
| 6,303,038 | B1 | 10/2001 | Sanders et al. |
| 6,447,722 | B1 | 9/2002 | Rakestraw |
| 6,576,674 | B2 | 6/2003 | Cutler et al. |
| 6,638,959 | B2 * | 10/2003 | Howarth et al. ............. 514/389 |
| 6,641,828 | B1 | 11/2003 | Howarth et al. |
| 6,881,418 | B2 * | 4/2005 | Morita et al. ............... 424/405 |

FOREIGN PATENT DOCUMENTS

| | | |
|---|---|---|
| EP | 1 263 685 A | 12/2002 |
| GB | 1358617 | 7/1974 |
| JP | 5631492 | 3/1981 |
| JP | 8176996 | 7/1996 |
| WO | 96/10541 | 4/1996 |
| WO | 01/55036 A2 | 8/2001 |

OTHER PUBLICATIONS

Chemical Abstracts, vol. 80, No. 20 (1973), Abstract No. 112498b.

Label for Lonza, Inc.'s DANTOBROM, EPA Reg. No. 6836-117, Approved on Jan. 18, 1985; Oct. 10, 2001; and Aug. 12, 2003, 12 pgs.

Label for Lonza, Inc.'s DANTOBROM, EPA Reg. No. 6836-115, Approved on Jun. 14, 1991; Jan. 21, 1992; Sep. 30, 1992; Oct. 30, 1996; Nov. 17, 1998; Nov. 2, 1999; Nov. 7, 2000; Mar. 12, 2001; Oct. 10, 2001; Oct. 3, 2002; Oct. 28, 2002; Aug. 12, 2003; Sep. 4, 2003; Oct. 23, 2003; Mar. 22, 2005; Nov. 16, 2005; and Feb. 28, 2007, 68pgs.

Petterson. R. C. and Crzeskowiak, V., "N-Halogen Compounds. I. Decomposition of 1,3-Dichloro-5,5-dimethylhydantoin in Water at pH 9," J. Org. Chem., 24, 1414 (1959), 6 pgs.

Corral, R. A. and Orazi, O. O., "Substitution in the Hydantoin Ring. III. Halogenation," J. Org. Chem., 28, 1100 (1963), 5 pgs.

Ludyanskiy, M. and Colby, S. J., "A Laboratory Method for Evaluating Biocidal Efficacy on Biofilms," Cooling Tower Institute, Paper TP96-07 (1996), 8 pgs.

Griebe, T. et al., "Analysis of Biofilm Disinfection By Monochloramine and Free Chlorine," Biofouling and Biocorrosion In Industrial Water Systems (edited by G. Geesey et al.), pp. 151-161, Lewis Publishers (1994).

Ludyanskiy, M. L. and Himpler, F. J., "The Effect of Haloganated Hydantoins on Biofilms," NACE, Paper 405 (1997), 11 pgs.

Elliot, A., "A Survey of Sludge Bulking and its Control in the Canadian Pulp and Paper Industry," Pulp & Paper Canada, 103:10 (2002), pp. 43-47.

Kuechler, T.C. et al., "Development of Monsanto's Towerbrom® Microbiocide, A New Bromine Microbiocide for Recirculating Water Systems," 1991 AWT COnference, Dec. 7, 1991, (24 pages).

Jolles, Z.E. Ed., "Bromine and its Compounds," Academic Press, New York, 1996, pp. 703-709.

Schulte, S. et al., "Efficacy of Biocides Against Biofilms," Chapter 5.1 in *Directory of Microbiocides for the Protection of Materials. A Handbook*. Ed. W. Paulus. Springer, (2004), pp. 93-120.

Ludensky, M.L., "An automated system for biocide testing on biofilms," *Journal of Industrial Microbiology and Biotechnology*, (1998) 20: 109-115.

Ludensky, M.L., "Control and monitoring of biofilms in industrial applications," *International Biodeterioration and Biodegradation*, (2003), 51: 255-263.

European Patent Office Action dated Mar. 6, 2008, which issued in the prosecution of European Patent Application No. 03814564.5, and which corresponds to the present application.

* cited by examiner

Figure 2. Testing biocidal efficacy of NaOBr

Figure 3. Testing biocidal efficacy of BCDMH/MEH

Figure 4. Testing biocidal efficacy of MCDMH

METHOD FOR REMOVAL OF BIOFILM

PRIORITY DATA

This application is a U.S. National Phase application of International Patent Application No. PCT/US2003/017882 filed Jun. 6, 2003, which claims priority from U.S. Provisional Application Ser. No. 60/435,680 filed Dec. 20, 2002, which is incorporated hereby by reference.

BACKGROUND OF THE INVENTION

Biofilm may be defined as an undesirable accumulation of microorganisms on a surface and in flocculent masses. It is estimated that more than 99% of all the planet's bacteria live in biofilm communities. Biofilm consists of cells immobilized in a substratum, frequently embedded in an organic polymer matrix of microbial origin, which can restrict the diffusion of substances and bind antimicrobials. In flowing aquatic environments, a biofilm consists of a sticky and absorptive polysaccharide matrix encompassing microorganisms. Biofilm bacteria are morphologically and metabolically distinct from free-floating bacteria. Their structural organization is a characteristic feature and distinguishes biofilm cultures from conventional planktonic organisms.

Biofilms create problems for industry from corroding water pipes to computer-chip malfunctions. Any man-made device immersed in an aquatic habitat is susceptible to colonization by microbial biofilm. For example, biofilm may be present on the surfaces of ship bottoms, industrial pipelines, household drains, and artificial hip joints. For the industrial manufacturer, biofilm clusters represent a source of microbial inoculation in a system and may cause plugging problems. In water treatment facilities, the formation of suspended biofilm produces a bulked biological sludge which settles poorly and is difficult to compact in the clarification process. Both non-filamentous and filamentous bulk forms are prevalent in which numerous bacteria permeate the floc. In addition to their role as fouling agents, biofilms may also have adverse effects on people, including altering their resistance to antibiotics and affecting the immune system. Thus, there exists a need in the art for developing effective methods of removing biofilm.

The dynamic nature of biofilms makes it difficult to measure and monitor biofouling. Biofilms often include embedded inorganic particles such as sediments, scale deposits, and corrosion deposits. Moreover, biofilms continuously change in thickness, surface distribution, microbial populations and chemical composition, and respond to changes in environmental factors such as water temperature, water chemistry and surface conditions. Thus, the complexity of biofilms has reduced the effectiveness of treatment and removal strategies.

Even though most microorganisms in industrial systems are associated with biofilm, they have historically received less attention than planktonic microorganisms. However, it has been shown that various biocides are less effective against biofilm than dispersed cells of the same organism. The most common biocides used in biofilm control are pure free halogen donors such as NaOCl and NaOCl/NaOBr. These, however, must be used in high quantities to be effective. In addition, several recent studies evaluating halogen efficacy on biofilms showed an increased disinfection resistance of attached bacteria to free chlorine. Free chlorine treatment at concentrations usually effective against planktonic microorganisms has little effect on the number of attached bacteria or on their metabolic activity. The data indicate that the transport of free chlorine into the biofilm is a major rate-limiting factor, and increasing concentrations did not increase biocidal efficiency. Griebe, T., Chen, C. I., Srinavasan, R., Stewart P., "Analysis of Biofilm Disinfection By Monochloramine and Free Chlorine," *Biofouling and Biocorrosion In Industrial Water Systems* (edited by G. Geesey, Z. Lewandowski, and H-C. Flemming), pp. 151-161, Lewis Publishers (1994).

Excessive reactivity of pure free halogen donors was overcome by using bromochlorodimethylhydantoin (BCDMH). The published study by M. Ludyansky and P. Himpler entitled "The Effect of Halogenated Hydantoins on Biofilms," NACE, Paper 405 (1997), demonstrated higher efficacy on biofilms compared to pure free halogen donors. However, while effective, it is still not an efficient halogen source when applied to biofilm.

Others have attempted to suppress biofilm growth in aquatic systems by using an oxidizing halogen with the addition of adjuvant. U.S. Pat. No. 4,976,874 to Gannon et al., incorporated herein by reference, discloses a method and formulation for the control of biofouling using an oxidizing halogen in combination with a non-oxidizing quaternary ammonium halide. However, this method poses environmental issues.

Thus, the control of biofilm in aquatic systems has typically involved the addition of oxidizing and non-oxidizing biocides to bulk water flow. However, high levels of these expensive chemicals are needed because their effectiveness is rapidly reduced as a result of exposure to the various physical and chemical conditions in specific applications since the concentration of the biocides is considerably reduced by the time the biocides reach the biofilm.

SUMMARY OF THE INVENTION

The present invention is directed to a method of disintegrating biofilm present in aqueous medium and controlling the odor attendant to its formation. The method comprises adding one or more chlorinated hydantoins, specifically, monochlorodimethylhydantoin (MCDMH) or dichlorodimethylhydantoin (DCDMH), to the aqueous medium. Of particular importance is that the chlorinated hydantoins' activity against biofilm is not lessened in the presence of sunlight, since the halogen-stabilized active chlorine solutions are strikingly photostable. The concentration of the chlorinated hydantoins maintained in the aqueous medium generally ranges from about 0.01 to about 100 ppm (expressed as $Cl_2$) for biofilm inhibition.

In a concentrate, the concentration of the chlorinated hydantoins generally ranges from about 0.1 up to 100% by weight based on the total weight.

The present invention has application to essentially all aqueous systems containing or having the potential to contain biofilm. These may be cooling water; pulping or papermaking systems, white water treatment, including those containing bulked activated sludge; and air washer systems; as well as agricultural potable and drainage systems; food preparation and cleaning systems; brewery, dairy and meat-producing systems; and oil industry systems. Aqueous systems also include any potable water systems, including drinking water systems; as well as recreational water systems, such as swimming pools and spas; household water-related systems, including toilet bowls, drains, sewers, shower stalls, bathtubs, and sinks; as well as institutional "water-related" systems, hospital systems, dental water systems and any system where a medical device is in contact with an aquatic medium; ornamental fountains, aquariums, fisheries, in aquaculture, and any other system subject to the growth of biofilm. The biofilm may comprise different forms and species of pathogenic microorganisms, e.g., *Legionella pneumophila*, adhered or not adhered to surfaces, such as mats, flocs and slime.

DETAILED DESCRIPTION OF THE INVENTION

The extent and nature of biofilm removal and disintegration, of course, vary with the context of the problem. The diverse nature of the problems and the diverse environments in which biofilms grow call for a variety of tactics and strategies for biofilm removal. With respect to an established biofilm, it is often desirable to remove it rather than to merely sterilize and leave it in situ. In addition, it may be important to kill the cells forming the biofilm and prevent them from spreading to other locations. Thus, for purposes of the present invention, the term "disintegration" of biofilm includes the removal and break-up of existing biofilm and the prevention of biofilm microorganism regrowth in a treated system. This is a more difficult task than "biofilm control" which includes both the prevention of biofilm growth from a clean system and the prevention of continued growth in a treated system upon which biofilm has already formed.

The term "chlorinated hydantoin" refers to an hydantoin which may be in the form of a pure compound, such as monochlorodimethylhydantoin or an admixture of hydantoins, i.e., monochlorodimethylhydantoin and dichlorodimethylhydantoin mixtures, or mixtures of hydantoins with degree of halogenation between 0.1 and 2.0.

The alkyl moieties of the chlorinated hydantoin may be the same or different, preferably alkyl groups having 1 to 6 carbon atoms.

Preferred chlorinated hydantoins include, but are not limited to, dichloro-5,5-dimethylhydantoin (DCDMH), monochloro-5,5-dimethylhydantoin (MCDMH), dichloro-5-methyl-5-ethylhydantoin (DCMEH), monochloro-5-methyl-5-ethylhydantoin (MCMEH), and any combination of any of the foregoing. The chlorinated hydantoin may be in the form of a solid, liquid, slurry, or gel. The term "solid" includes powders, granules, tablets, briquettes and slurries.

Concentrates of the chlorinated hydantoin have concentrations of active ingredients greater than typical biofilm control concentrates. For example, a solid concentrate of chlorinated hydantoin typically contains 70% by weight of active ingredient (expressed as $Cl_2$) based upon 100% total weight of concentrate. In contrast, liquid concentrates of sodium hypochlorite typically comprise only about 12% by weight of active ingredient based upon 100% total weight of concentrate. Additionally, the chlorinated hydantoins of the present invention are stable, unlike most bleaches currently sold.

While the above discussion refers to the treatment of an aqueous system containing biofilm with the chlorinated hydantoin, it is also contemplated that the aqueous system be formed after a dry biofilm or biofilm in a non-aqueous medium is brought in contact with a solid or granular halogenated hydantoin. In such instance, the aqueous system may be formed by the addition of water or water vapor to the two solids or water-free materials.

The amount of the chlorinated hydantoin added to the aqueous medium is sufficient to disintegrate the biofilm. This is generally from about 0.01 to about 100 ppm (expressed as $Cl_2$), preferably from about 0.05 to about 25 ppm (expressed as $Cl_2$).

In addition to adding the pre-formed halogenated hydantoin to the aqueous system, it may be desirable to form the halogenated hydantoin in situ. This can be done by adding an hydantoin and an halogenating agent to the biofilm containing aqueous system separately in the appropriate molar ratio. For example, an alkali metal hypochlorite (e.g., NaOCl) or chlorine gas or another active chlorine source and dimethylhydantoin can be added in a molar ratio sufficient to form in situ the desired amount of the halohydantoin. Broadly, the molar ratio of chlorine (from the chlorine source) to alkylated hydantoin is from 1:100 to 100:1, preferably from 1:10 to 10:1.

In some systems, such as cooling water systems, additives are always used. In other systems, such as swimming pools, there may be no performance additives.

Performance additives (i.e., compositions that enhance the quality and use of the chlorinated hydantoins) include, but are not limited to, cleaning agents, biodispersants, solubility modifiers, compaction aids, fillers, surfactants, dyes, fragrances, dispersants, lubricants, mold releasers, detergent builders, corrosion inhibitors, chelants, stabilizers, bromide sources, and scale control agents. An important requirement is that the material be compatible with the chlorohydantoin composition.

Solubility modifiers which may be added to chlorinated hydantoins described herein include, for example, sodium bicarbonate, aluminum hydroxide, magnesium oxide, barium hydroxide, and sodium carbonate. See U.S. Pat. No. 4,537,697. Solubility modifiers can be used in the compositions in an amount ranging from 0.01% to 50% by weight.

Examples of compaction aids are inorganic salts including lithium, sodium, potassium, magnesium, and calcium cations associated with carbonate, bicarbonate, borate, silicate, phosphate, percarbonate, and perphosphate. See U.S. Pat. No. 4,677,130. Compaction aids can be used in the compositions in an amount ranging from 0.01% to 50% by weight.

Fillers which may be added to the chlorohydantoins include, for example, inorganic salts, such as lithium, sodium, potassium, magnesium and calcium cations with sulfate, and chloride anions, as well as other inorganics such as clays and zeolites. Fillers are used in compositions to reduce product costs and can be added in an amount ranging from 0.01% to 50% by weight.

The biodispersant enhances the efficacy of the chlorinated hydantoin as a biofilm control agent and assists in maintaining the surfaces of the container in which the aqueous medium is contained clean. They are typically surfactants and preferably surfactants with a non-biocidal effect on microorganisms and biofilms. Examples of biodispersants include Aerosol OTB (sodium dioctyl sulfosuccinate), disodium lauryl sulfosuccinate, sodium lauryl sulfoacetate, as well as other sulfonates. Surfactants are used in the compositions to enhance cleaning performance and can be added in an amount ranging from 0.01% to 20% by weight. Generally, such a mixture contains from about 80% to about 99.99% by weight of chlorinated hydantoin and from about 0.01% to about 20% by weight of biodispersant, based upon 100% total weight of mixture; preferably, from about 90 to about 99.99% by weight of chlorinated hydantoin and from about 0.01% to about 10% by weight of biodispersant.

An aqueous solution of the desired non-chlorinated hydantoin(s) at the desired mole ratios may be prepared by the methods described in U.S. Pat. No. 4,560,766, and Petterson, R. C., and Grzeskowiak, V., J. Org. Chem., 24,1414 (1959) and Corral, R. A., and Orazi, O. O., J. Org. Chem., 28, 1100 (1963), both of which are hereby incorporated by reference.

EXAMPLE 1

Biofilm Inhibition Control Efficacy

The efficacy of biocides and biocides with dispersants was estimated by a reduction of biofilm dry weight in test flasks, compared to untreated controls. Biofilm development was determined gravimetrically by the methods described in Ludyansky, M., Colby, S., *A Laboratory Method for Evaluating Biocidal Efficacy on Biofilms,* Cooling Tower Institute, Paper TP96-07 (1996).

The sheathed *Sphaerotilus natans* (ATCC 15291), which is known to be very resistant to any chemical control and found in a variety of applications (cooling water systems, paper process waters, and sewage treatment processes), was used in the tests.

The bacteria were cultivated at 25-30° C. in a 5% CGY medium which contained: 5 g of casitone (Difco), 10 g of glycerol, and 1 g of yeast autolysate (Difco) per liter of DI water. The inocula contained approximately $10^6$ cells per milliliter. 8 oz. flasks were filled with 150 ml of 5% CGY media and 1 ml of *Sphaerotilus natans* inoculum. The flasks were filled with the test biocides, namely, NaOCl, NaOBr, MCDMH. Additional flasks, not containing a biocide, served as controls. The flasks were installed on a shaker and maintained at 22-30° C. rotating at 100-200 rpm for 48-72 hours. The contents were dried for 5 hours at 105° C. and cooled overnight. The difference between the weight of the flasks containing the dried biomass and the tare weight of the flasks represented the dry biofilm mass.

The effectiveness of biofilm prevention was calculated as a percent change in growth based on the difference between the average dried biofilm weight in the untreated controls and in the treated flasks, according to the following formula:

$$E\% = (B_{control\ avg} - B_{avg})/B_{control\ avg} * 100,\ \text{where E}$$
%=percent reduction of biofilm growth,
B=Biofilm weight, and $B_{control}$=Biofilm weight in the control flask.

The results of the experiments, including the concentration of the biocides, are set forth in Table 1:

TABLE 1

| Biocide | Concentration, ppm | B avg, g | B control avg, g | E, % |
|---|---|---|---|---|
| NaOCl | 10 | 0.0028 | 0.0185 | 84.86 |
| NaOBr | 10 | 0.0013 | 0.0185 | 92.97 |
| MBDMH | 10 | 0.0008 | 0.0185 | 95.7 |
| MCDMH | 10 | 0.0005 | 0.0185 | 97.3 |
| DCDMH | 10 | 0.0005 | 0.0173 | 97.1 |
| NaOCl | 5 | 0.009 | 0.0144 | 37.5 |
| NaOBr | 5 | 0.0021 | 0.0144 | 85.4 |
| MBDMH | 5 | 0.0081 | 0.0152 | 46.7 |

TABLE 1-continued

| Biocide | Concentration, ppm | B avg, g | B control avg, g | E, % |
|---|---|---|---|---|
| MCDMH | 5 | 0.0007 | 0.0144 | 95.1 |
| DCDMH | 5 | 0.0009 | 0.0173 | 94.8 |

The results show that chlorinated hydantoin (MCDMH) was a superior biofilm inhibition agent over free halogen donors (NaOCl or NaOBr).

EXAMPLE 2

Biofilm Removal Control Efficacy

*Sphaerotilus natans* (ATCC 15291), as in Example 1, was used in the tests described below.

Biofilm Test System

An on-line testing system for chlorinated biocide efficacy testing was used to provide a real-time, non-destructive method for biofilm monitoring and measurement. The system monitors the heat transfer resistance (HTR) which correlates to biofilm formation and accumulation, and dissolved oxygen (DO) level in the bulk water which correlates with changes in biofilm activity. The system design, parameters and growth conditions are disclosed in Ludensky, M., "An Automated System for Biocide Testing on Biofilms." *Journal of Industrial Microbiology and Biotechnology,* 20:109-115 (1998).

The system consisted of a continuous-flow heat-exchange loop, a biological growth reactor (chemostat) and subsystems for life support, biofilm measurement, and environmental control. All system parameters, including water flow, temperature, dilution rate and nutrient concentration, were optimized for obtaining fast, heavy and reproducible biofilm growth. The system make-up water was kept at constant oxygen saturation (by continuous sparging of air), temperature, and pH conditions. Thus, any changes in DO concentrations or pH levels in the recirculating water were considered due to biofilm activity. All monitoring and control parameters were calculated in the data acquisition system, which was controlled by a custom-designed computer software program. Data was collected every 15 seconds, with averages calculated and recorded every 3 to 60 minutes in a spreadsheet for subsequent graphical analysis. The program was designed so that the system was able to function continuously under constant conditions for several weeks. Biocide efficacy testing was conducted through analysis and comparison of the shape and values of the corresponding curves of HTR and DO. Analysis included consideration of curve patterns corresponding to biocide treatment, as well as biofilm recovery (regrowth).

Growth Conditions

The sheathed *Sphaerotilus natans* (ATCC 15291), known to form a tenacious biofilm on heat exchanger surfaces in cooling water systems and papermaking machines, was selected for biofilm growth. Inocula were pumped into the microbial growth reactor and allowed to sit at room temperature overnight. The next day, make-up water and nutrient (CGY media) were added. Selection of initial growth conditions and parameters of the system was based on previous experience, laboratory limitations, geometric size of the system's components, and the desire to promote a growth of biofilm. Shifting of growth conditions from planktonic growth to attached filamentous growth was obtained by lowering media concentrations to less than 5% and maintaining dilution rates higher than maximum specific rate. Test conditions are shown in Table 2.

TABLE 2

Bioflim System On-Line Test Conditions

| Parameter | Conditions |
|---|---|
| pH | 7.2-8.5 |
| Temp., circulating water | 74-76° F. |
| Temp., wall | 85° F. |
| Makeup water | Clinton tap |
| Substrate concentration | CGY; 30-70 ppm |
| Inoculum | *S. natans* |
| Water flow | 3 fps |
| Dilution rate | 0.9 |
| Make up water | 170 ml/min |
| Nutrient addition | 1 ml/min |
| System volume | 10 liters |

Biocidal efficacy of the test solutions was determined by analysis of the shape of the HTR and DO curves indicating the biofilm's response to biocidal treatments.

Treatment Programs

During treatment programs, the system was continuously fed with nutrient and make-up water (constant chemistry, oxygen and temperature). Three modes of treatments were tested, namely, slug, slug plus continuous, and continuous.

Slug treatment was conducted by the addition of a prepared stock solution in a precalculated dose (per volume of the circulating water in the system) to the chemostat. In the slug plus continuous mode, biocide treatment was carried out by an initial slug dose injected to overcome halogen demand, followed by a continuous, 3-hour treatment at a constant concentration based upon the makeup water rate.

Biocide Preparation and Monitoring

All five biocides, NaOCl, NaOBr, MCDMH, BCDMH/MEH, and DCDMH, were prepared as 1000 ppm fresh $Cl_2$ master solutions. Treatment concentrations for all biocides were calculated from the measurement of free and total residual halogen, as measured by the DPD $Cl_2$ test, conducted immediately before treatment.

Figure 1:
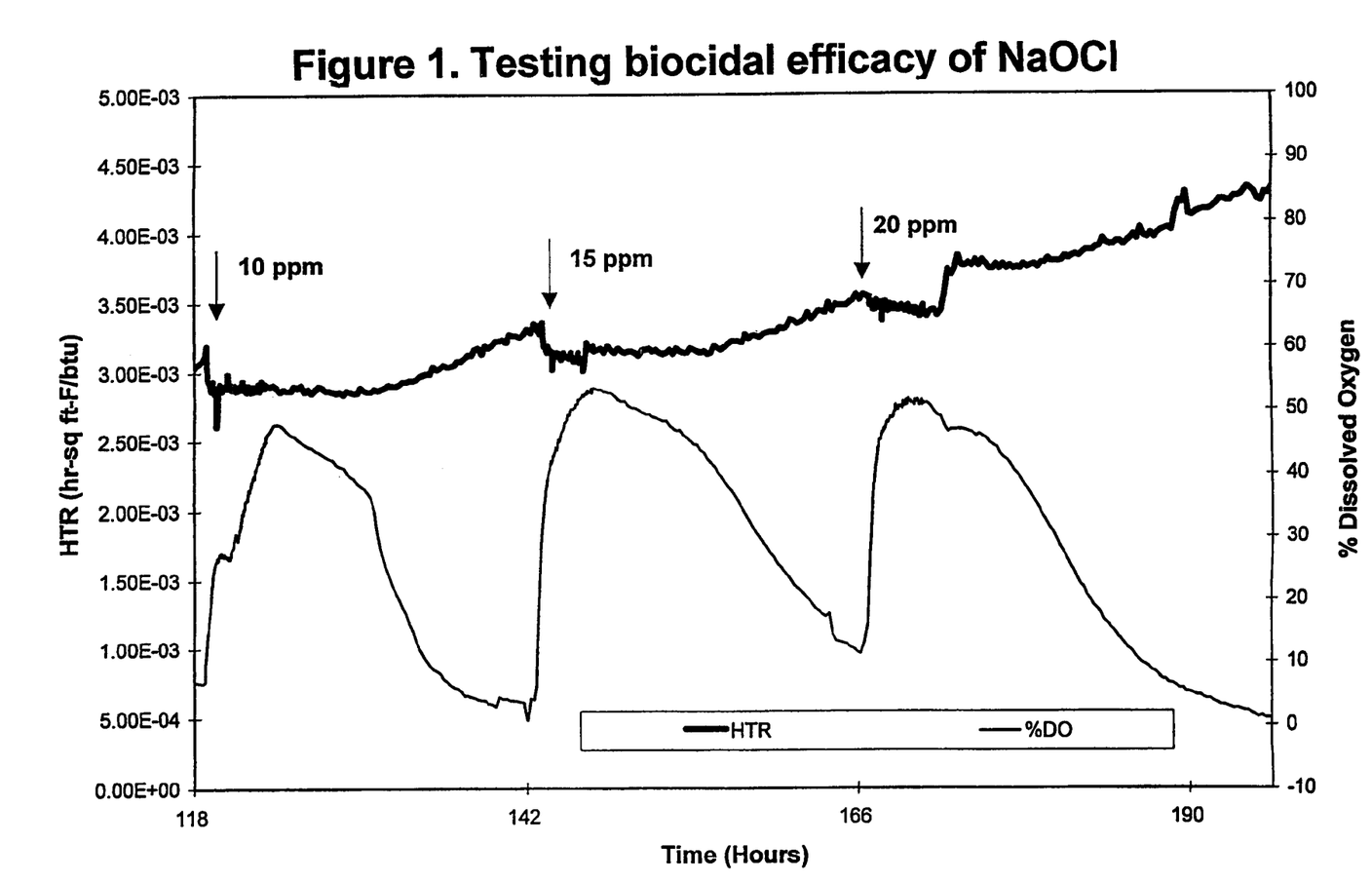
FIG. 1 illustrates the effect of NaOCl on heat transfer resistance (HTR) which correlates to biofilm formation and accumulation and dissolved oxygen (DO) level in an aqueous system.
Figure 2:
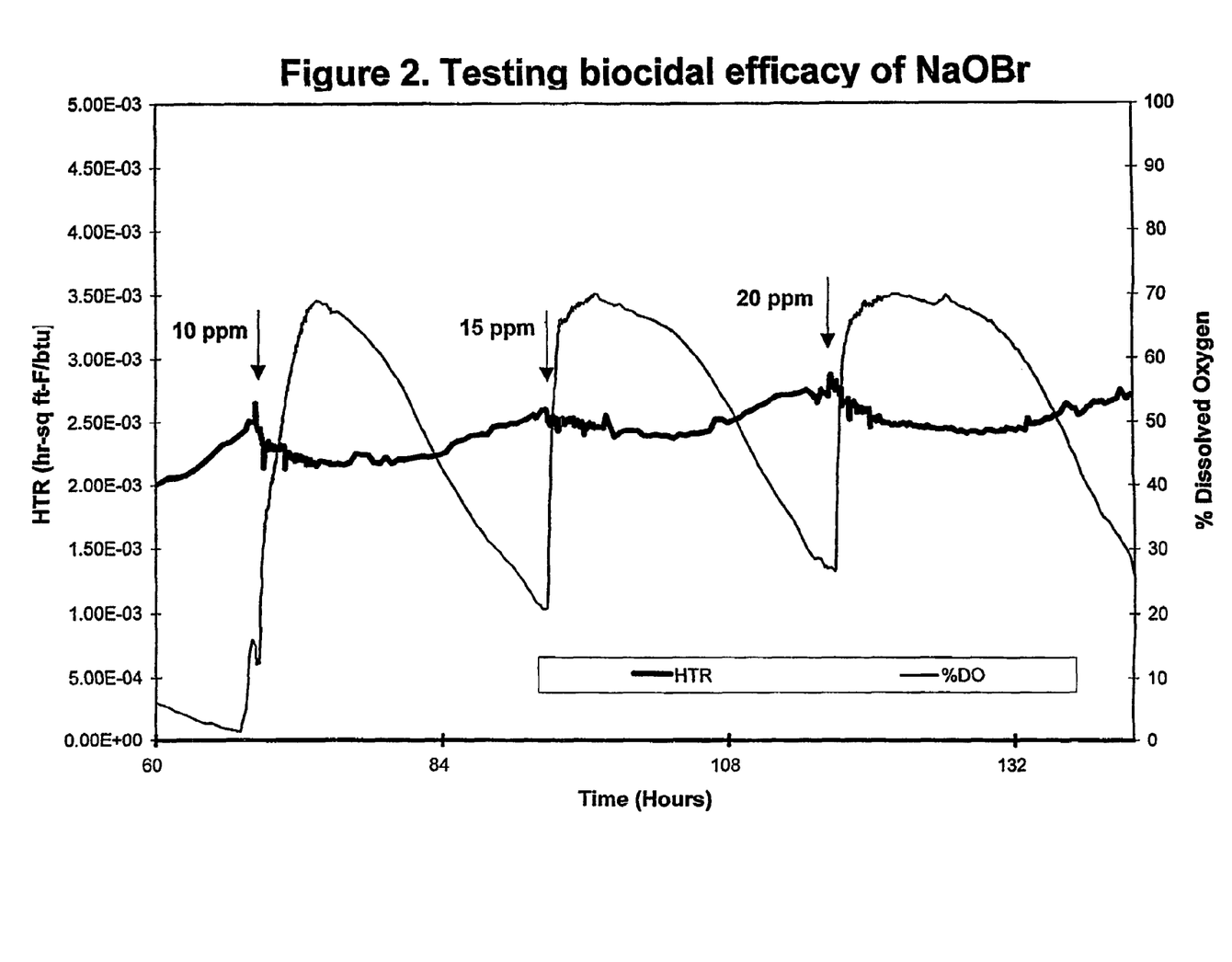
FIG. 2 illustrates the effect of NaOBr on heat transfer resistance (HTR) and dissolved oxygen (DO) level in an aqueous system.
Figure 3:
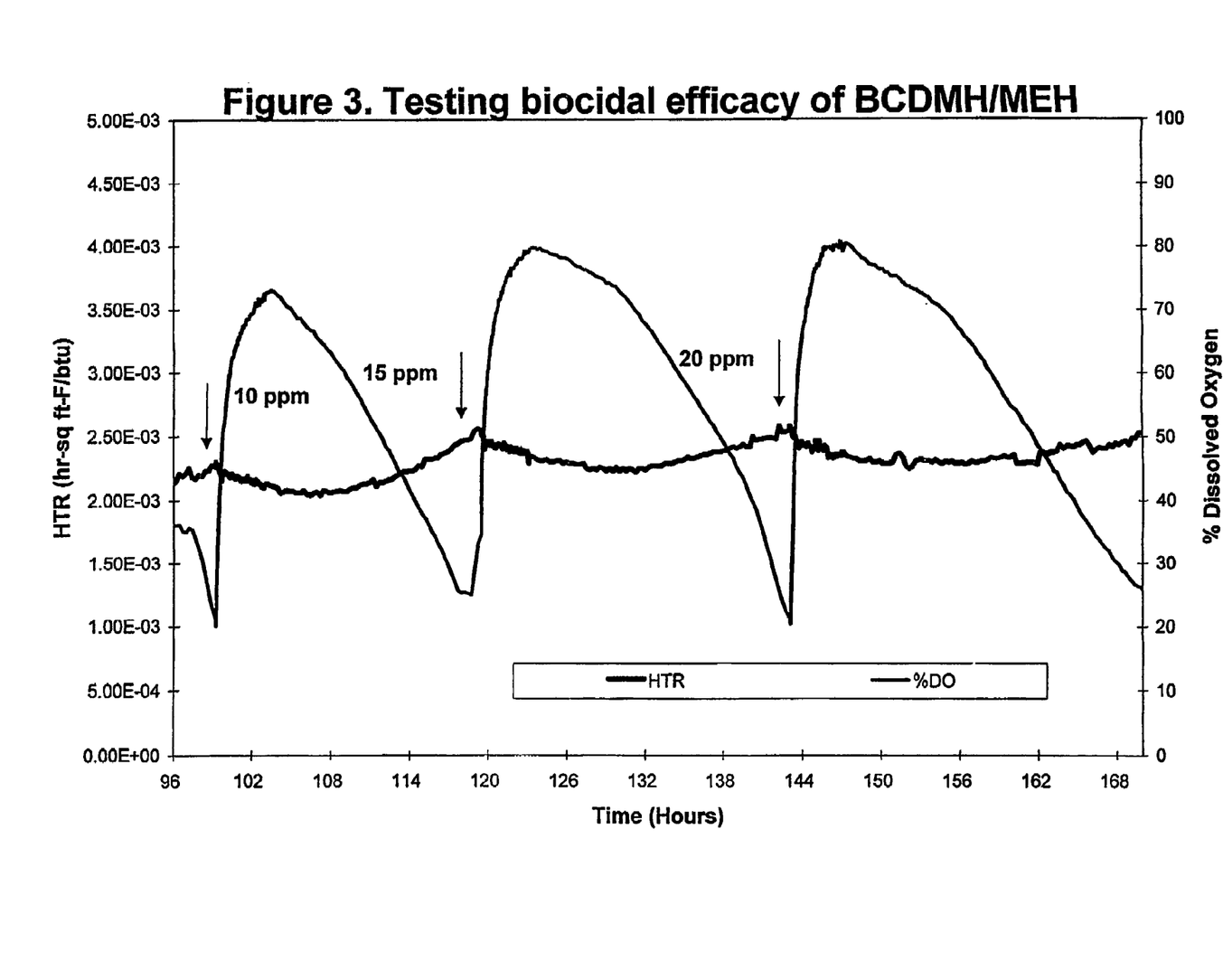
FIG. 3 illustrates the effect of BCDMH/MEH on heat transfer resistance (HTR) and dissolved oxygen (DO) level in an aqueous system.

Tests incorporating repeated slug plus continuous treatments at increasing initial concentrations (10, 15 and 20 ppm) were performed for three consecutive days on NaOCl, NaOBr, MCDMH, BCDMH/MEH, and DCDMH. Heat transfer rate and dissolved oxygen levels in the system were automatically monitored and their dynamics were analyzed. Based on obtained parameters, the following conclusions were reached:

NaOCl, NaOBr, and BCDMH/MEH were not able to remove biofilm at any of the tested concentrations. Biofilm recovery was observed 24 hours after the start of each treatment and HTR values were higher than values observed at the start of each treatment, as shown in FIGS. 1, 2 and 3.

Dissolved oxygen response to biocide treatment was the strongest in the case of DCDMH, and the weakest in the case of NaOCl. Through analysis of curve patterns (FIG. 1-FIG. 5), it was concluded that biofilm regrowth control could be achieved by a slug plus continuous treatment of 15 ppm BCDMH/MEH or 20 ppm of NaOBr as shown in FIG. 2 and FIG. 3. However, neither of these biocides was able to initiate biofilm removal.

Testing of chlorinated hydantoins MCDMH and DCDMH demonstrated a unique effect: biofilm sloughing occurred soon after addition of 20 ppm of either MCDMH or DCDMH.

Figure 4:
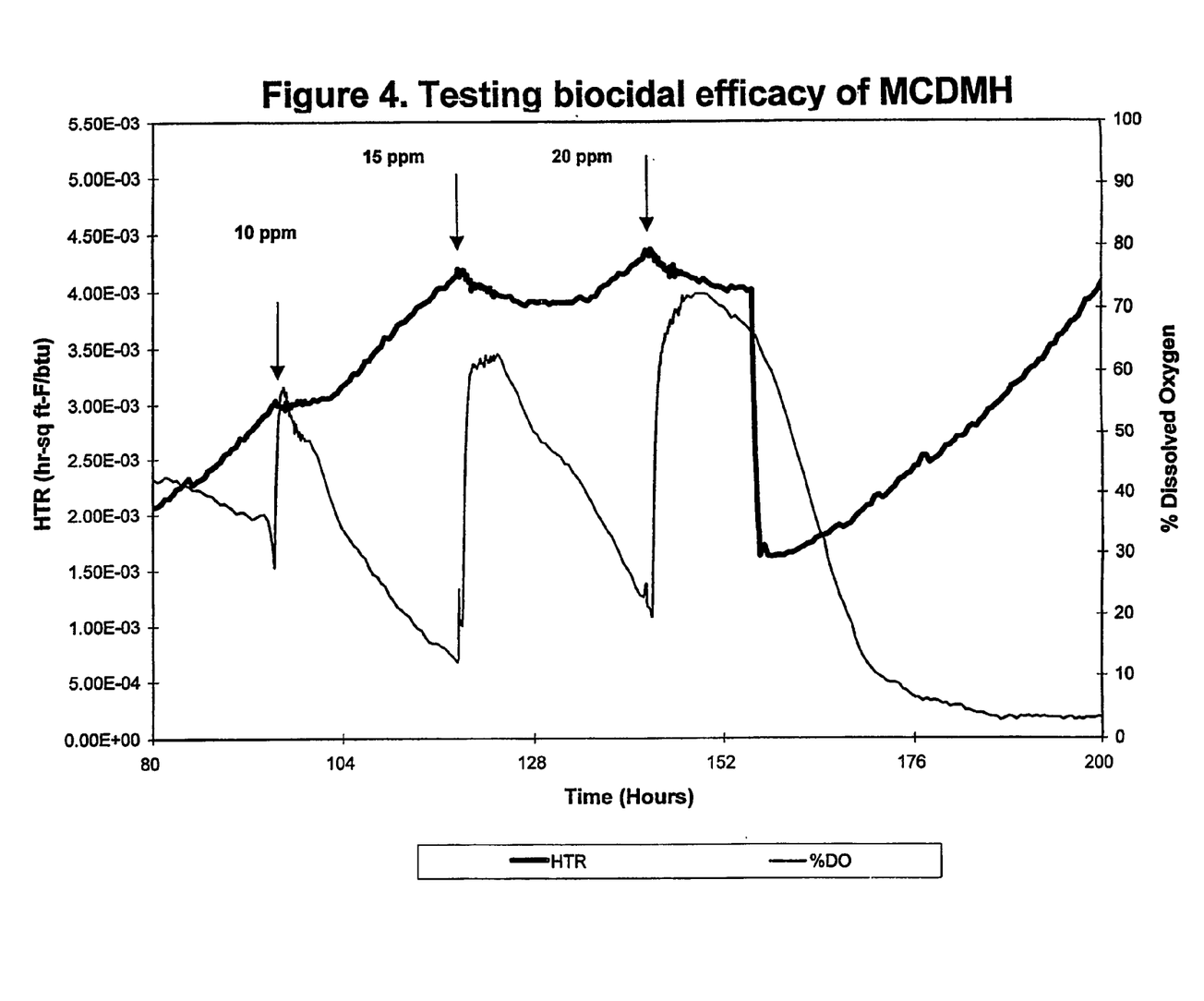
FIG. 4 illustrates the effect of MCDMH on heat transfer resistance (HTR) and dissolved oxygen (DO) level in an aqueous system.
Figure 5:
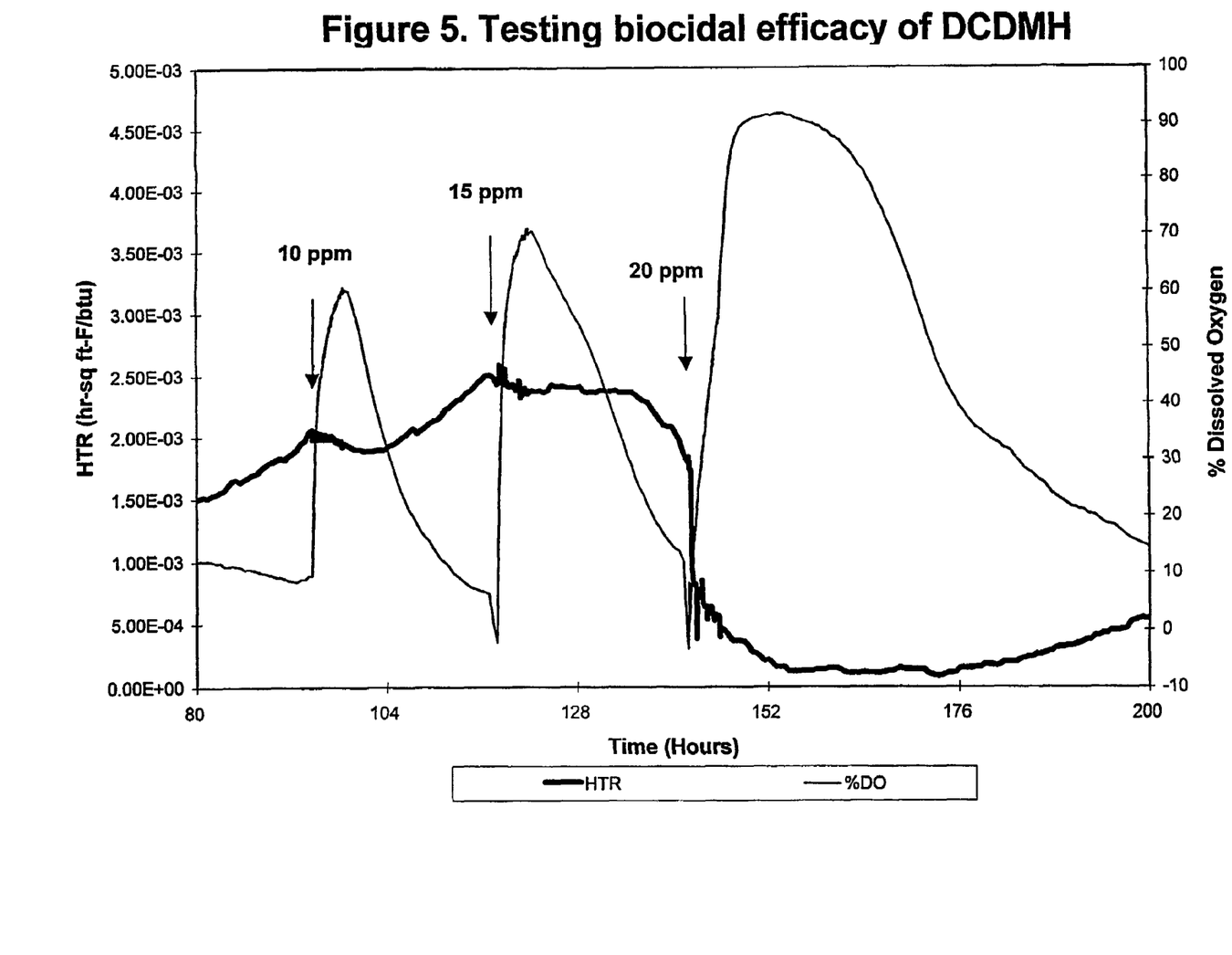
FIG. 5 illustrates the effect of DCDMH on heat transfer resistance (HTR) and dissolved oxygen (DO) level in an aqueous system.

The results of the tests are shown in FIG. 4 and FIG. 5. This effect is not common for any other oxidizing biocides.

The observations set forth above are summarized in the following table:

TABLE 3

Slug Plus Continuous Treatment

| | Biofilm Control | | Biofilm Removal |
|---|---|---|---|
| | HTR | DO | HTR |
| NaOCl | Not effective | Weakest | No |
| NaOBr | Effective at 20 ppm | Moderate | No |
| BCDMH/MEH | Effective at 15 ppm | Moderate | No |
| MCDMH | Effective at 15 ppm | Moderate | Yes at 20 ppm |
| DCDMH | Effective at 15 ppm | Strongest | Yes at 20 ppm |

EXAMPLE 3

This example demonstrates the enhanced photostability of MCDMH as compared to NaOCl when test solutions thereof are exposed to simulated sunlight.

Test solutions were prepared by adding to tap water having a temperature of 22° C. and a pH of 7.8 NaOCl and MCDMH at the concentrations indicated in Table 4 below. These solutions were illuminated by UVA-340 fluorescent lights that simulate the spectral radiance of the sun at the surface of the earth. The test samples were covered with quartz plates, transparent to ultraviolet light, to prevent evaporation. Total halogen concentrations were measured as a function of time. The generated active halogen decay curves were analyzed using first order kinetic algorithms and the corresponding active halogen half-lives calculated. The results are shown in Table 4.

As shown in Table 4, MCDMH provides dramatically superior photostability to NaOCl. The observed active halogen half-life for MCDMH was 108 hours compared to 1.1 hour for NaOCl.

TABLE 4

Photolysis of MCDMH and NaOCl Solutions

| | Total Halogen (ppm as $Cl_2$) | |
|---|---|---|
| Delta Time (hr) | NaOCl | MCDMH |
| 0 | 4.0 | 5.9 |
| 1.5 | 1.1 | 5.6 |
| 6.5 | 0.07 | 5.3 |
| 29.5 | — | 4.1 |
| 52.5 | — | 3.1 |
| 100 | — | 2.3 |
| 187 | — | 1.5 |
| 267 | — | 1.0 |
| First order half-life (hr) | 108 | 1.14 |

These data clearly show that the activity of MCDMH dropped negligibly for the first 6.5 hours and significant activity remained for the duration of the test, while the NaOCl's activity dropped precipitously in the presence of the simulated sunlight. The comparative half-lives further show the remarkable photostability of the chlorinated hydantoin.

EXAMPLE 4

Hydantoin-stabilized active chlorine solutions can likewise be generated by combining hydantoins with NaOCl. As shown in Table 2, combinations of DMH and NaOCl produce greater photostability than even combinations with cyanuric acid, a well-known chlorine photostabilizer for the recreational water market. The test conditions were the same as those of Example 3.

TABLE 5

Photostability of Hydantoin and Cyanuric Acid Stabilized Hypochlorite Solutions

| | Total Halogen (ppm as $Cl_2$) | |
|---|---|---|
| Delta Time (hr) | NaOCl + 30 ppm DMH | NaOCl + 30 ppm Cyanuric acid |
| 0 | 4.6 | 4.3 |
| 1.5 | 4.3 | 4.1 |
| 6.5 | 4.05 | 3.6 |
| 29.5 | 3.6 | 2.0 |
| 52.5 | 3.0 | 0.78 |
| 100 | 2.2 | 0.07 |
| 187 | 1.68 | — |
| 267 | 1.19 | — |
| First order half-life (hr) | 141 | 17 |

The data in Table 5 show that DMH dramatically enhances the photostabilization of NaOCl and the combination performs better that the NaOCl and cyanuric acid. The observed active halogen half-life for the NaOCl+DMH stabilized solution was 141 hours as compared to 17 hours for cyanuric acid stabilized NaOCl.

What is claimed is:

1. A method of disintegrating biofilm in an aqueous system, which comprises adding to or forming in an aqueous medium of the aqueous system containing the biofilm a chlorinated hydantoin comprising a monochlorodialkylhydantoin, dichlorodialkylhydantoin or a mixture thereof in an amount sufficient to disintegrate the biofilm and remove the biofilm from surfaces in said aqueous system, wherein the alkyl group of the chlorinated hydantoin contains from 1 to 6 carbon atoms.

2. The method of claim 1, wherein the chlorinated hydantoin is monochlorodimethylhydantoin, dichlorodimethylhydantoin, or a mixture thereof.

3. The method of claim 1, wherein the chlorinated hydantoin is added to the aqueous medium as a solution or an aqueous slurry.

4. The method of claim 1, wherein the chlorinated hydantoin is added to the aqueous medium as a solid.

5. The method of claim 1, wherein the treated aqueous medium is exposed to sunlight.

6. The method of claim 1, wherein the chlorinated hydantoin is formed in situ by adding to the aqueous medium chlorine from a chlorine source and an alkylated hydantoin in a molar ratio of chlorine to alkylated hydantoin of from 1:100 to 100:1.

7. The method of claim 6, wherein the molar ratio of chlorine to alkylated hydantoin is from 1:10 to 10:1.

8. The method of claim 1, wherein the aqueous medium contains biofilm adhering to a substrate.

9. The method of claim 1, wherein the chlorinated hydantoins are added with performance additives.

10. The method of claim 9, wherein the performance additives are dispersants, biodispersants, scale control agents, corrosion inhibitors, surfactants, biocides, cleaning agents, and mixtures thereof.

11. The method of claim 1, wherein the aqueous system is a cooling water system, a pulping or papermaking system, an air washer system, an agricultural potable and drainage system, a food preparation or cleaning system, an oil industry system, a potable water system, a household water-related system, or an institutional water-related system.

12. The method of claim 1, wherein the chlorinated hydantoins are in an amount sufficient to form a concentration of from about 20 ppm to about 100 ppm (expressed as $Cl_2$) of the chlorinated hydantoins in the aqueous medium.

13. The method of claim 1, wherein the chlorinated hydantoin is dichloro-5,5-dimethylhydantoin (DCDMH), monochloro-5,5-dimethylhydantoin (MCDMH), dichloro-5-methyl-5-ethylhydantoin (DCMEH), monochloro-5-methyl-5-ethylhydantoin (MCMEH), or a mixture thereof.

14. The method of claim 1, wherein the aqueous system is a system subject to the growth of biofilms.

15. A method of removing biofilm from a substrate in an aqueous medium which comprises: adding to or forming in said aqueous medium monochlorodimethylhydantoin, dichlorodimethylhydantoin, or a mixture thereof in an amount sufficient to remove the biofilm from the substrate in the aqueous medium.

16. The method of claim 15, wherein the chlorinated dimethylhydantoin is formed in situ by adding to the aqueous medium chlorine from a chlorine source and dimethylhydantoin in a molar ratio of chlorine to dimethylhydantoin of from 1:10 to 10:1.

17. The method of claim 16, wherein the chlorine source is sodium hypochlorite or gaseous chlorine.

\* \* \* \* \*